(12) United States Patent
Miller et al.

(10) Patent No.: US 8,043,252 B2
(45) Date of Patent: Oct. 25, 2011

(54) NITRIC OXIDE DECONTAMINATION OF THE UPPER RESPIRATORY TRACT

(75) Inventors: Christopher Miller, North Vancouver (CA); Alex Stenzler, Yorba Linda, CA (US)

(73) Assignees: Sensormedics Corporation, Yorba Linda, CA (US); Pulmonox Technologies Corporation, Edmonton, Alberta (CA)

( * ) Notice: Subject to any disclaimer, the term of this patent is extended or adjusted under 35 U.S.C. 154(b) by 977 days.

(21) Appl. No.: 12/004,514

(22) Filed: Dec. 20, 2007

(65) Prior Publication Data
US 2008/0173311 A1 Jul. 24, 2008

Related U.S. Application Data

(60) Division of application No. 11/107,618, filed on Apr. 14, 2005, now Pat. No. 7,335,181, which is a continuation-in-part of application No. 11/021,109, filed on Dec. 23, 2004, now Pat. No. 7,122,018, which is a continuation-in-part of application No. 10/944,479, filed on Sep. 17, 2004, now Pat. No. 7,892,198, which is a continuation of application No. 10/172,270, filed on Jun. 14, 2002, now Pat. No. 6,793,644, which is a continuation of application No. 09/749,022, filed on Dec. 26, 2000, now Pat. No. 6,432,077.

(51) Int. Cl.
*A61M 37/00* (2006.01)
*A61M 1/00* (2006.01)
*A01N 59/02* (2006.01)

(52) U.S. Cl. .......... 604/23; 604/290; 604/289; 604/540; 604/543; 424/718

(58) Field of Classification Search .................. 604/289, 604/290; 424/45, 718
See application file for complete search history.

(56) References Cited

U.S. PATENT DOCUMENTS

| 5,725,492 | A |   | 3/1998  | Igo et al.      |            |
|-----------|---|---|---------|-----------------|------------|
| 6,019,100 | A | * | 2/2000  | Alving et al.   | 128/203.12 |
| 6,142,147 | A | * | 11/2000 | Head et al.     | 128/204.21 |

FOREIGN PATENT DOCUMENTS
WO        WO 00/30659        6/2000
* cited by examiner

*Primary Examiner* — Jacqueline F. Stephens
(74) *Attorney, Agent, or Firm* — Arent Fox, LLP

(57) ABSTRACT

A method of topically treating the respiratory tract of a mammal with nitric oxide exposure includes the steps of providing a source of nitric oxide containing gas and delivering the nitric oxide containing gas nasally to the upper respiratory tract of the mammal. Also provided are several designs for a nasal delivery device for the controlled nasal deliver the nitric oxide containing gas.

23 Claims, 4 Drawing Sheets

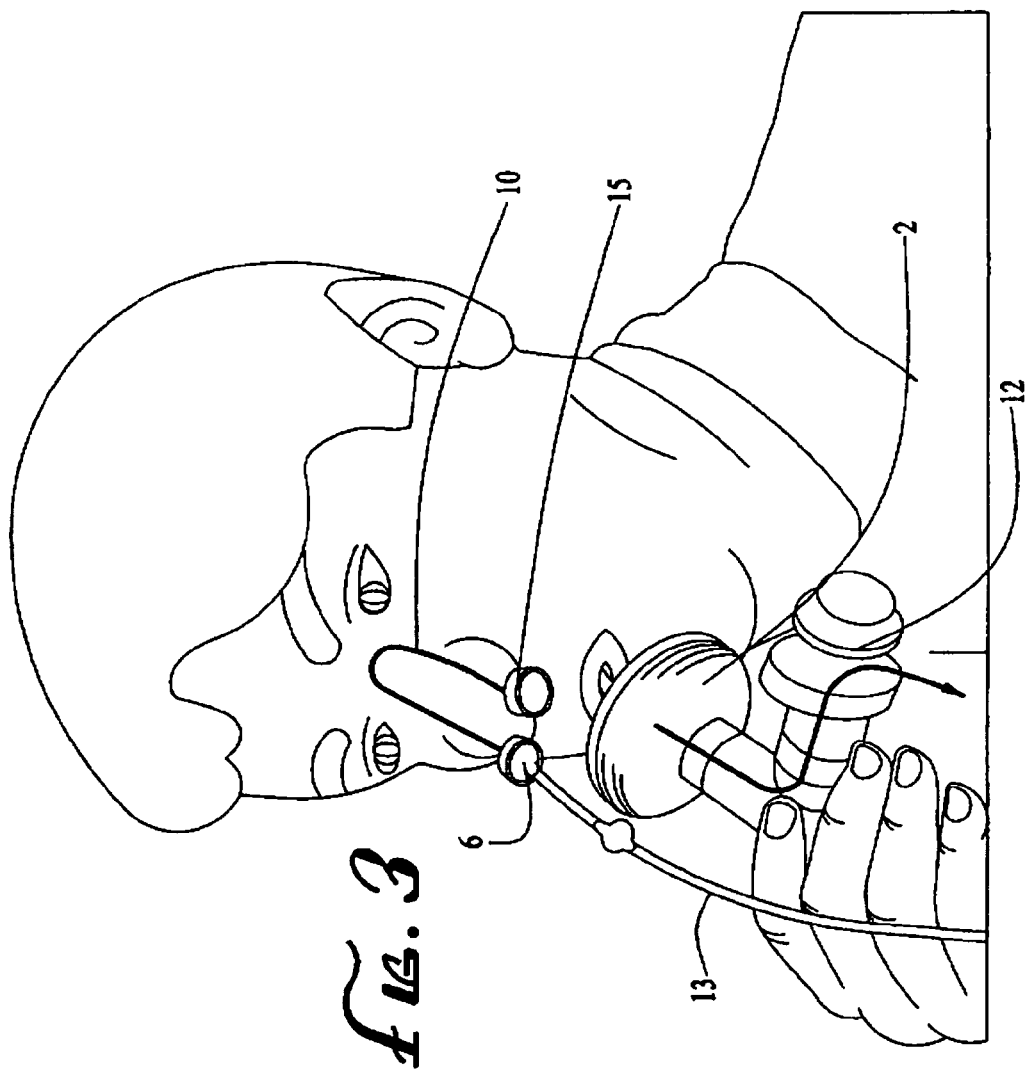

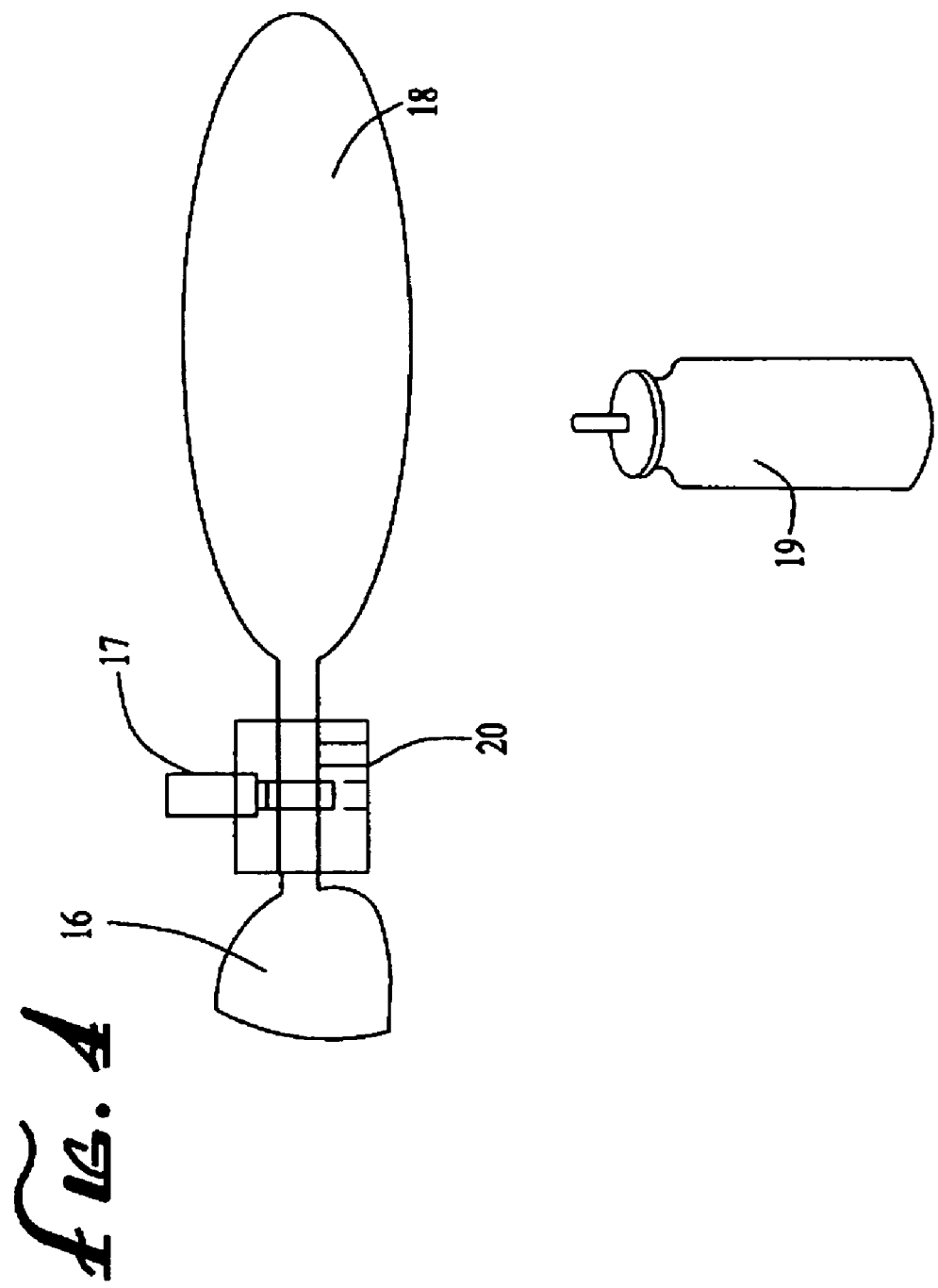

NITRIC OXIDE DECONTAMINATION OF THE UPPER RESPIRATORY TRACT

CLAIM OF PRIORITY

This application is a divisional of U.S. patent application Ser. No. 11/107,618, filed on Apr. 14, 2005, now U.S. Pat. No. 7,335,181 which is a continuation-in-part of U.S. patent application Ser. No. 11/021,109, filed on Dec. 23, 2004, now U.S. Pat. No. 7,122,018 which is a continuation-in-art of U.S. application Ser. No. 10/944,479, filed Sep. 17, 2004, now U.S. Pat. No. 7,892,198 which is a continuation of U.S. application Ser. No. 10/172,270, filed Jun. 14, 2002 and issued as U.S. Pat. No. 6,793,644, which in turn is a continuation of U.S. application Ser. No. 09/749,022, filed on Dec. 26, 2000 and issued as U.S. Pat. No. 6,432,077. The above patents and patent applications are incorporated by reference as if set forth fully herein.

FIELD OF THE INVENTION

The field of the invention relates to devices and methods for topically treating the upper respiratory tract of a mammal. More specifically, it relates to devices and methods for controlled delivery of the nitric oxide containing gas nasally to the upper respiratory tract of the mammal to topically treat the respiratory tract and to decontaminate the upper respiratory tract of microorganisms.

BACKGROUND OF THE INVENTION

The upper respiratory tract is the entrance port for microorganisms entering the lower respiratory tract, i.e., the lungs of a subject. The upper respiratory tract frequently traps these microorganisms and may kill them before they effectively enter the body. However, if the microorganism is able to get a foothold in the upper respiratory tract (e.g., a common cold virus), it is possible that the virus may thereafter move into the lungs. Additionally, the existence or persistence of microorganisms in the upper respiratory tract may lower the immune system so that the lungs become susceptible to another microorganism such as bacteria that may cause a bacterial pneumonia or other infection. Therefore, targeted therapeutic or preventative treatment of the upper respiratory tract would speed the recovery from local infections or preclude the progression to an infection in the lungs or other related systems.

The link between upper respiratory tract infections and the lower respiratory tract is well documented. For example, the following articles, each herein incorporated by reference in their entirety, support the proposition that treating the upper respiratory tract has beneficial value to the lungs and lower respiratory tract. Papadopoulos, et al. "Rhinoviruses infect the lower airways." J. Infect. Dis. 2000; 181:1875-1884; Gern J. E. "Viral respiratory infection and the link to asthma." Pediatr. Infect. Dis. J. 2004; 23 (Suppl. 1):S78-S86; Fraenkel, et al "Lower airway inflammation during rhinovirus colds in normal and in asthmatic subjects." Am. J. Respir. Crit. Care Med. 1995: 151:879-886; and Pizzichini, et al. "Asthma and Natural Colds. Inflammatory Indices in Induced Sputum: A Feasibility Study." Am J. Respir. Crit. Care Med. 1998; 158: 1178-84.

The treatment of the upper respiratory tract has focused primarily on traditional pharmaceuticals, such as orally consumed antibiotics. In the 1980's, it was discovered by researchers that the endothelium tissue of the human body produced nitric oxide (NO), and that NO is an endogenous vasodilator, namely, an agent that widens the internal diameter of blood vessels. NO is most commonly known as an environmental pollutant that is produced as a byproduct of combustion. At low concentrations, researchers have discovered that inhaled NO can be used to treat various pulmonary diseases in patients. For example, NO has been investigated for the treatment of patients with increased airway resistance as a result of emphysema, chronic bronchitis, asthma, adult respiratory distress syndrome (ARDS), and chronic obstructive pulmonary disease (COPD). NO has also been shown to have anti-microbial and/or microcidal activity over a broad range of microorganisms.

While NO has shown promise with respect to certain medical applications, delivery methods and devices must cope with certain problems inherent with gaseous NO delivery. First, exposure to high concentrations of NO maybe toxic, especially exposure to NO in concentrations over 1000 ppm. Even lower levels of NO, however, can be harmful if the time of exposure is relatively high. For example, the Occupational Safety and Health Administration (OSHA) has set respiratory tract exposure limits for NO in the workplace at 25 ppm time-weighted averaged for eight (8) hours.

Another problem with the delivery of NO is that NO rapidly oxidizes in the presence of oxygen to form $NO_2$, which is highly toxic, even at low levels. If the delivery device contains a leak, unacceptably high levels of $NO_2$ gas can develop. In addition, to the extent that NO oxidizes to form $NO_2$, there is less NO available for the desired therapeutic effect. The rate of oxidation of NO to $NO_2$ is dependent on numerous factors, including the concentration of NO, the concentration of $O_2$, and the time available for reaction. Since NO will react with the oxygen in the air to convert to $NO_2$, it is desirable to have minimal contact between the NO gas and the outside environment.

Accordingly, there is a need for a device and method for the topical treatment of upper respiratory tract by the administration of gaseous NO. The delivery must be take into account subject respiration, comfort, and safety. In addition, delivery methods and devices may be designed to target delivery of the NO gas to the upper respiratory region of the patient without allowing the introduction of NO to the lungs.

SUMMARY OF THE INVENTION

One embodiment of the invention is a method of topically treating a respiratory tract of a mammal with nitric oxide exposure comprising the steps of: (1) providing a source of nitric oxide containing gas; and (2) nasally delivering the nitric oxide containing gas, wherein the nitric oxide containing gas is confined to an upper respiratory tract of the mammal. The upper respiratory tract includes the nasal cavities, sinuses and nasopharynx. Another embodiment is a method of topically decontaminating an upper respiratory tract of microorganisms with nitric oxide exposure comprising the same two steps. The microorganisms may include, but is not limited to, bacteria, viruses, fungi, and parasites. Another embodiment is a method of bathing an upper respiratory tract of a mammal with nitric oxide containing gas comprising the same two steps.

Several delivery mechanisms correlate the administration of the NO containing gas with either the patient's inhalation or exhalation. Additionally, delivery may be correlated to the patient's nasal or oral breathing. The delivery methods act to isolate the NO containing gas within the upper respiratory tract of the mammal. The nasal delivery may also coincide with a deceleration of the mammal's nasal inhalation. The delivery may occur at a predetermined time after a detection of a mammal's inhalation or at a predetermined time after a detection of a mammal's exhalation.

The concentration of nitric oxide in the nitric oxide containing gas may be about 120 ppm to about 400 ppm, preferably, about 160 ppm to about 220 ppm. The source of nitric oxide containing gas may be a pressurized cylinder containing nitric oxide gas. In several methods, the volume of nitric oxide containing gas nasally delivered substantially equals the volume of gas that fills the nasopharynx of the mammal. In other methods, the rate of the delivering of the nitric oxide containing gas is about 1 liter per minute.

Delivery may be accomplished by bolus or pulse injections, and a series of injections over a period of time may be supplied to suitably bathe the nasopharynx with a therapeutic amount of NO containing gas.

The delivery may be controlled in that it occurs when the soft palate of the mammal is in a closed position. The closing of the soft palate may be induced by a resistive element in communication with the oral cavity of the mammal.

The mammal may nasally inhale from a controllable reservoir of nitric oxide containing gas. This reservoir may have a volume that is substantially equal to the volume of a mammal's nasopharynx. The reservoir may be connected to a nasal mask or nasal insert prongs for delivery to the mammal.

Several nasal delivery devices are herein described. Delivery may be accomplished through a nasal device, wherein one nostril of the mammal receives the nitric oxide containing gas while the other nostril of the mammal is fitted with a one-way valve. Such devices may include nasal insert prongs, mouthpieces, tubing, control valves, NO containing gas source and/or nasal masks.

In one embodiment, a nasal delivery device for controllably delivering a nitric oxide containing gas to an upper respiratory tract of a mammal may include: (1) a source of nitric oxide containing gas; (2) a nasal interface adapted to provide fluid communication between the source of nitric oxide containing gas and a first nostril of the mammal; (3) a flow-control valve for controlling the flow of the nitric oxide containing gas from the source to the mammal; (4) a one-way valve operable to be inserted into a second nostril of the mammal; and (5) a mouthpiece comprising a resistive element operable to close the soft palate of the mammal.

The nasal delivery device may also include a pressure monitor operable to detect a pressure within an oral cavity of the mammal. The supply unit of the nasal delivery device may blend a source gas with compressed air to obtain the gaseous substance to be delivered. The nasal delivery device may include an analyzer to detect ambient or delivered levels of a gaseous concentration. The nasal delivery device may deliver about 1 liter per minute of the gaseous substance. The one-way valve may restrict inward flow upon delivery of the gaseous substance and allow the gaseous substance to exit the upper respiratory tract.

Another nasal delivery device for controllably delivering a nitric oxide containing gas to an upper respiratory tract of a mammal may include: (1) a collapsible reservoir comprising nitric oxide containing gas and having a volume substantially equal to the volume of the nasopharynx of the mammal; (2) a nasal interface adapted to provide fluid communication between a nose of the mammal and the collapsible reservoir; and (3) a control valve for controlling the delivery of the nitric oxide containing gas from the collapsible reservoir to the nasal interface. The nasal interface may be either a nasal mask operable to be placed around the nose of the mammal or a nosepiece operable to be inserted into at least one nostril of a mammal. The collapsible reservoir may hold about 20 mL to about 50 mL of nitric oxide containing gas.

Another nasal delivery device for controllably delivering a gaseous substance to an upper respiratory tract of a mammal, may include: (1) a source of breathable gas connected via tubing to a nasal interface for providing a gas stream of breathable gas to the mammal nasally; (2) an inspiration flow profile sensor that measures the inspiration flow profile of the inspiration breath of the mammal; (3) a source of nitric oxide containing gas operably in fluid communication with the gas stream of the breathable gas; (4) a flow controller located between the source of nitric oxide containing gas and the gas stream for releasing nitric oxide containing gas to the nasal interface; and (5) a controller for triggering the release of nitric oxide containing gas to the nasal interface at a predetermined time close to the end of the mammal's inspiration and at a flow rate that confines the nitric oxide containing gas in the upper respiratory tract of the mammal.

BRIEF DESCRIPTION OF THE DRAWINGS

FIG. 3 illustrates an embodiment of another device to deliver NO containing gas to the upper respiratory tract of a patient.

FIG. 4 illustrates an embodiment of another device to deliver NO containing gas to the upper respiratory tract of a patient.

DETAILED DESCRIPTION OF THE PREFERRED EMBODIMENTS

Figure 1:
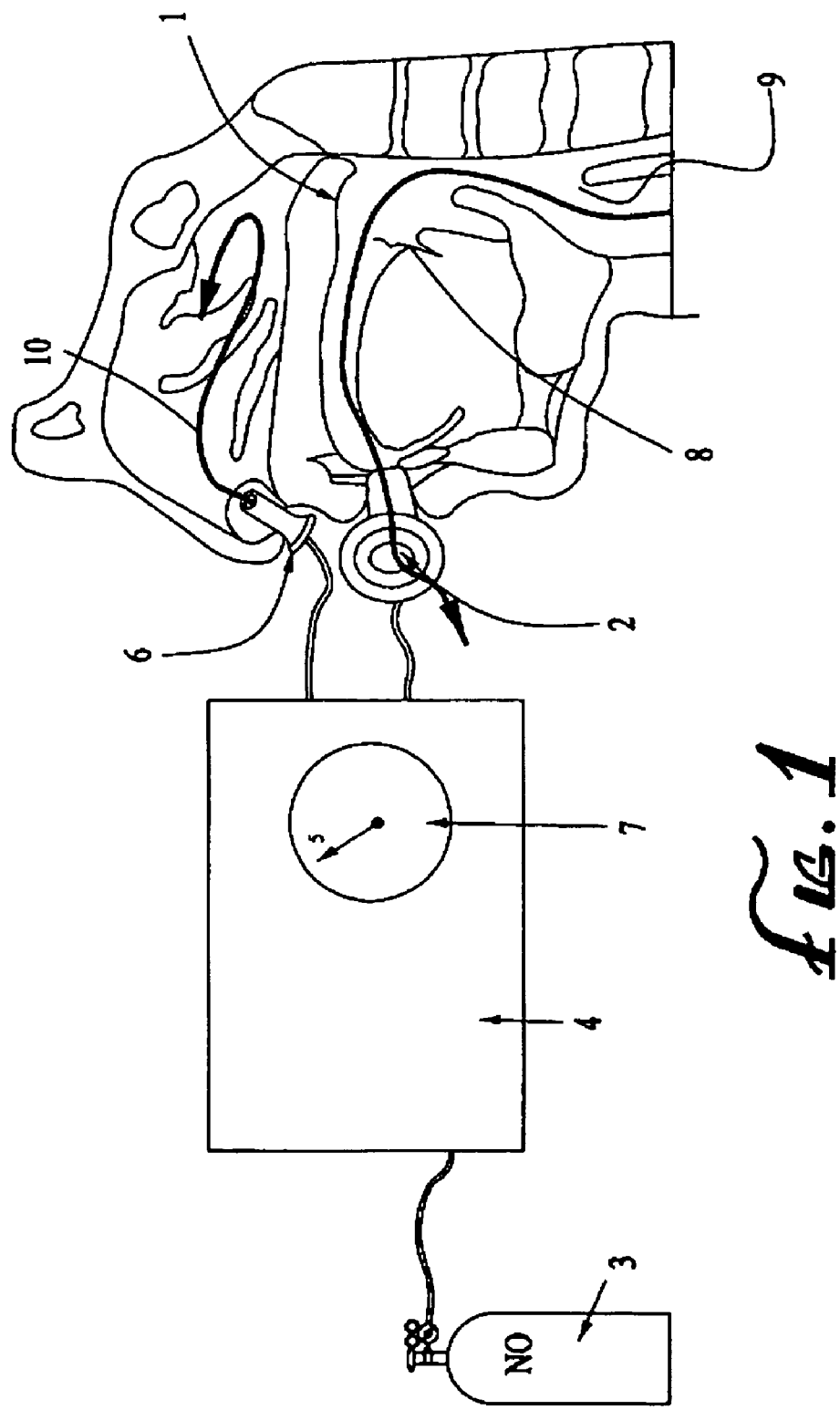
FIG. 1 illustrates the delivery of nitric oxide containing gas to the upper respiratory tract of a human subject.

Before the present compositions and methods are described, it is to be understood that this invention is not limited to the particular devices, compositions, methodologies or protocols described, as these may vary. It is also to be understood that the terminology used in the description is for the purpose of describing the particular versions or embodiments only, and is not intended to limit the scope of the present invention which will be limited only by the appended claims.

Although any methods, devices, and materials similar or equivalent to those described herein can be used in the practice or testing of embodiments of the present invention, the preferred methods, devices, and materials are now described. All publications mentioned herein are incorporated by reference. Nothing herein is to be construed as an admission that the invention is not entitled to antedate such disclosure by virtue of prior invention. As used herein, terms such as "subject," "patient," and "mammal" may be used interchangeable.

The nasal airway is comprised of two nasal cavities separated by the nasal septum and includes numerous ostia, such as the paranasal sinus ostia and the tubal ostia, and olfactory cells. The nasal airway can communicate with the nasopharynx, also described as the upper throat area, the oral cavity, and the lower airway, with the nasal airway being in selective communication with the anterior region of the nasopharynx and the oral cavity by opening and closing of the oropharyngeal velum, or often referred to as the soft palate. The closing of the soft palate is achieved by providing a certain positive pressure in the oral cavity, such as achieved on exhalation through the oral cavity against a resistive element.

The methods described herein provide nasal delivery of a nitric oxide containing gas to the upper respiratory tract including the nasopharynx. By use of the term "upper respiratory tract," Applicants are referring to the area defined from the entrance of the nostrils to the soft palate, the area including the nasal cavities, sinuses and nasopharynx. The methods and devices described herein controllably deliver the nitric oxide containing gas nasally. By "controllably", it is meant that the nitric oxide containing gas is confined to the upper respiratory tract of the mammal.

The methods for controllably delivering nitric oxide containing gas to the upper respiratory tract may be achieved by a number of different ways. For example, the delivery of nitric oxide gas may be timed with a nasally inhaled gas stream such that it is delivered only at the end of the subject's inhalation. This timing of nitric oxide containing gas delivery causes the nitric oxide containing gas to reach only the upper respiratory airway, and not further into the respiratory system. Alternatively, the oropharyngeal velum or soft palate may be induced to close to seal the upper respiratory airway from the rest of the lower respiratory system, including the lungs. Delivery of nitric oxide containing gas can then be made to this sealed upper respiratory airway. One way to induce closing of the soft palate is through the natural exhalation of the subject through the mouth against partially closed lips. Preferably, a resistive element is provided to the subject's mouth such that more precise increases in pressure in the oral cavity is provided.

Because NO containing gas is only delivered to the upper respiratory system, there are minimal toxicity concerns in using the contemplated therapeutic concentrations of nitric oxide gas (such as 160 ppm to 400 ppm). Previous delivery methods for gaseous NO to a patient have allowed the NO containing gas to flow directly or indirectly into the lungs. In the present applications, since the NO containing gas does not reach the lungs, there is less absorption of the nitric oxide into the blood stream to form methemoglobin. Concern about damage to the lungs resulting from conversion of NO to $NO_2$ is also decreased.

Accordingly, concentrations greater than 100 ppm nitric oxide and, more preferably, greater than 160 ppm nitric oxide may be safely bathe the upper respiratory tract of a subject. Preferably, the concentration of nitric oxide in the nitric oxide containing gas in the upper respiratory tract is about 120 ppm to about 400 ppm, more preferably, about 160 ppm to about 220 ppm.

Preferred Delivery During Exhalation

In one embodiment, NO containing gas may be nasally delivered to a subject during exhalation. As seen in FIG. 1, this method uses exhaling through the mouth against a resistive element 2 to close the soft palate 1, sealing the nasopharynx from the rest of the lower respiratory system. While a patient exhales through the oral cavity, a flow-control valve may then be opened to administer the NO containing gas from a nitric oxide gas source through one of the nostrils of the patient. Since the soft palate is closed (by the mechanism of exhalation), this delivery of NO containing gas is confined to the upper respiratory tract including the closed or sealed nasopharynx.

Figure 2:
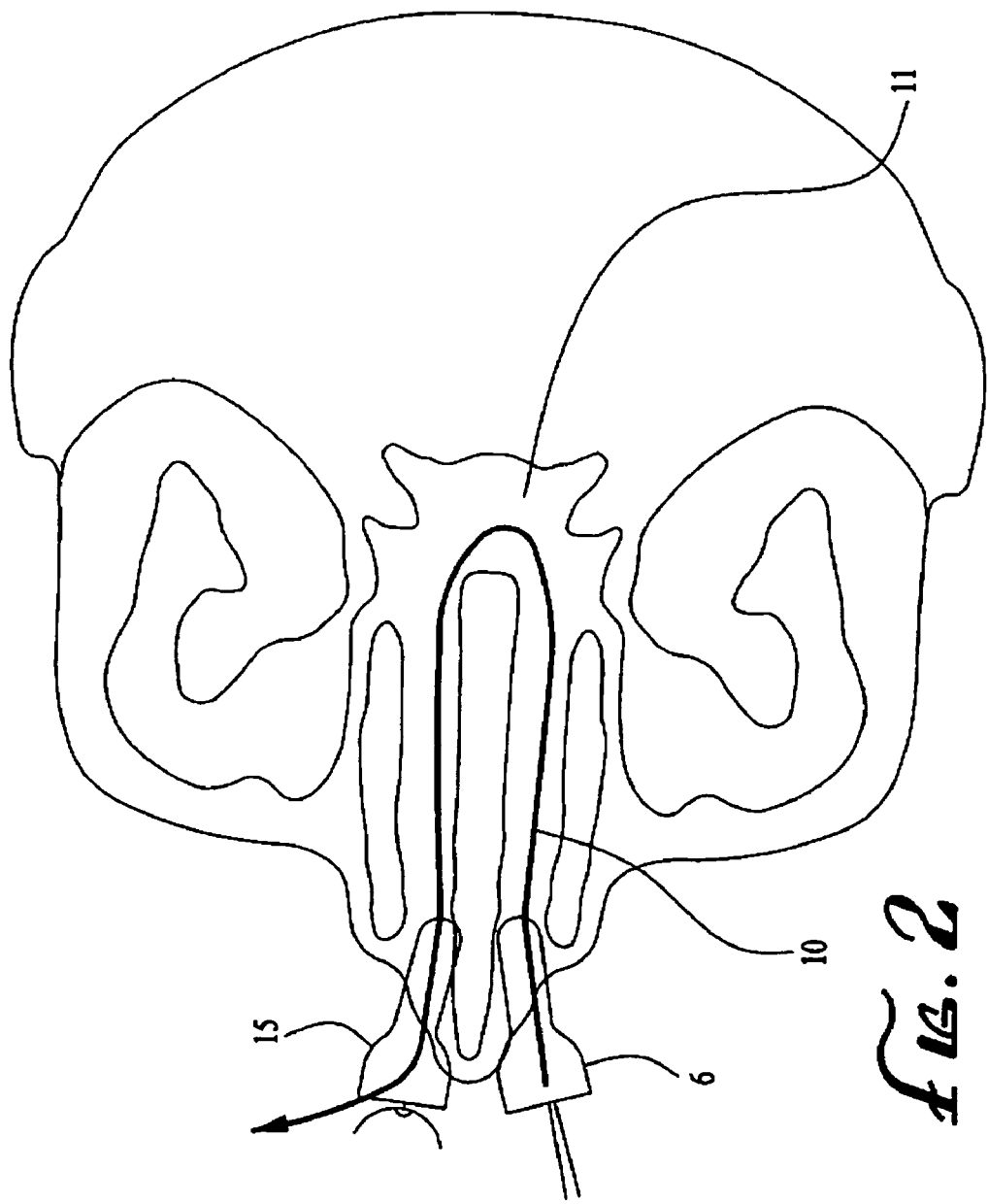
FIG. 2 is a top cross sectional view of a human head, illustrating the flow of nitric oxide containing gas bathing the nasal cavities, according to one embodiment of the present invention.

A pressure monitor 7 for monitoring the oral cavity may also be provided. Once a pressure monitor of a resistor element (monitoring the oral cavity pressure and thus the position of the soft palate) is present (and reaches a threshold such as about 5 cm $H_2O$), the flow of NO containing gas may begins. The flow of NO containing gas is preferably delivered through one nostril using a nasal interface comprising a valve 6 while the other nostril may be sealed with a one-way flow out valve 15 (FIG. 2). The pressure of the delivered NO gas may be just above atmospheric, such as about 1-4 cm $H_2O$. The pressure of the NO gas however should be lower than about 5 cm $H_2O$, so that the soft palate remains in a closed position. The one-way valve 15 seals the nostril from inhaling air, and thus, prevents outside air from carrying the NO containing gas in the nasopharynx into the lungs. However, air and NO containing gas are allowed to exit through the one-way valve 15.

As seen in FIGS. 1 and 2, blocking one nostril creates a controlled system wherein the NO containing gas bathes the closed nasopharynx and the nasal cavity of the patient, before it exits through the one-way valve. These delivery systems cause the nitric oxide gas to enter into one nasal cavity, flow around the posterior margin into the sealed nasopharynx 11, out of the nasopharynx, and out the other nasal cavity. The flow of the NO containing gas is represented by the reference number 10 in FIGS. 1-3.

The exit of the NO containing gas through the one-way valve 15 may be into the atmosphere. Because the volume of NO containing gas is relatively small (about 1 liter per minute), allowing this gas to be exited freely into the atmosphere does not create a substantial risk of harm to the patient and surrounding environment. Ambient concentrations of nitric oxide or nitrogen dioxide resulting from the use of a delivery system is estimated at about 50 ppb. To illustrate the safety of the exiting NO containing gas, a comparison to the concentration of nitric oxide in cigarette smoke may be appropriate. It is estimated that a similar volume of exhaled cigarette smoke contains about 150 ppm of NO. Therefore, allowing the exit of the NO containing gas into the atmosphere through the one-way valve 15 is significantly less harmful, than exhaled cigarette smoke released into the atmosphere.

Still referring to FIGS. 1 and 2, the one-way valve 15 also acts to prevent NO containing gas to enter the lower respiratory tract 9. A patient is unable to inhale air back through the one-way valve 15. Therefore, once the NO containing gas is turned off, and the NO containing gas is bathing the upper respiratory tract, there is little risk of this gas reaching the lungs. If the patient inhales through its mouth while the NO containing gas is within the upper respiratory tract, and thus opens the soft palate 1, the NO containing gas will not flow into the lower respiratory tract from the upper respiratory tract because there is no flow of air into the nasal cavity to displace the NO containing gas. The only pathway for gas entrance into the lungs is through the oral cavity. This pathway is represented by the reference number 8 in FIG. 1. Thus, a patient's inhalation will be oral and the absence of nasal flow will contain the NO containing gas in the upper respiratory area. Because there is no nitric oxide delivery through the oral cavity, no nitric oxide enters the lungs during this patient inhalation.

FIG. 1 further illustrates a nasal delivery device which may be used to nasally deliver the NO containing gas while a subject is exhaling. This device may include a nasal interface 6 for fitting to a nostril of a subject, a one-way valve 15 to block the outlet nostril of a subject, a mouthpiece 2 through which the subject in use exhales and that includes a resistive element, and a NO gas source 3 and control unit 4 for regulating and monitoring the concentration and flow of nitric oxide gas. Additionally, a pressure monitor 7 may also be provided (either integral to the NO control unit 4 or as a separate unit) to monitor the pressure of the oral cavity. The NO delivery unit is preferably computer controlled via a controller such as a microprocessor. However, discrete electronic or pneumatic components could accomplish the same objective. Logic (either through firmware or software) may be programmed in order to control the delivery of NO such that delivery of NO gas from the NO gas source is triggered when the oral cavity reaches a certain threshold pressure, as measured by the pressure monitor. Thus, the pressure monitor provides feedback to the delivery unit as to when the NO gas is to be released into the nasal airway. If the pressure in the oral cavity drops below the threshold, then the soft palate is no longer closed and the logic is programmed to stop the NO gas flowing into the nasal cavity.

Still referring to FIG. 1, the NO gas source 3 may be a pressurized cylinder containing NO gas. Appropriate systems and methods for storing and using NO containing gas, diluting it to effective concentrations and channeling it to a delivery device are known in the art, and are described, for example, in U.S. Pat. Nos. 6,793,644 and 6,581,599, which are hereby incorporated by reference as if fully set forth herein. These systems and methods may be used with any delivery device described herein.

While the use of a pressurized cylinder is the preferred method of storing the NO containing gas source, other storage and delivery means, such as a dedicated feed line (wall supply) can also be used. The NO containing gas may be adjusted for NO concentration by use of a diluent gas as described in U.S. Pat. No. 6,793,644 or the NO containing gas may be supplied in its desired concentration without the need for dilution. The source of diluent gas may contain $N_2$, $O_2$, Air, an inert gas, or a mixture of these gases. The source of diluent gas may be stored within a pressurized cylinder or provided by a simple air pump. For example, compressed clean, dry air at 50 psig may be blended with the NO source gas. Both the NO gas source and the diluent source may include internal or external filters, such as a particulate filter, a watertrap filter, or a combination thereof. Because the topically applied gas is not inhaled, there is no need for it to contain oxygen as one of its components.

The NO gas from the NO gas source 3 and the diluent gas from the diluent gas source preferably pass through pressure regulators to reduce the pressure of gas that is admitted to the control unit 4 and delivered to the subject. The respective gas streams may also pass via tubing to an optional gas blender to mix the respective gases. The NO containing gas may be output from the gas blender and travel via tubing to a flow control valve, preferably contained in the control unit 4. The flow control valve may include, for example, a proportional control valve that opens (or closes) in a progressively increasing (or decreasing if closing) manner. As another example, the flow control valve may include a mass flow controller. The flow control valve controls the flow rate of the NO containing gas that is introduced to the nasal interface 6. The NO containing gas leaves the flow control valve via flexible tubing. The flexible tubing attaches to an inlet in the nasal interface 6.

Additionally, NO and $NO_2$ analyzers, which are known in the art, may also be incorporated into the control unit 4 to monitor the NO and $NO_2$ concentration of the gas delivered to the subject's upper respiratory tract.

The nasal interface 6 may include one nasal insert prong that fits into one of the nostrils of the patient, providing a tight sealing fit. The nasal insert prong may be oval or cylindrical in shape, may include a flange design to hold the insert within the nostril, and may be shaped to fit coaxially within the nostril of a patient. Such a suitable nasal insert prong may be the nasal inserts described for use in the LYRA® Interface, available from VIASYS Healthcare Inc., Conshohocken, Pa. An appropriate nasal interface is one that is made of a soft, flexible material and provides an effective sealing of the nostril. In addition to insert prongs, a nasal pillow of other suitable design may be used. The nasal interface 6 may be formed of a resilient material such as a polymeric or silicone elastomer material. The nasal interface 6 may include an optional one-way valve that prevents the backflow of gas into the tubing. The other nostril of a patient may be fitted with a one-way flow-out valve 15 to control the targeted delivery of the NO containing gas to the sealed upper respiratory tract. This one way flow-out valve 15 may also be constructed as an integral part of the nasal interface or as a separate piece from the nasal interface.

When the patient breathes out through a mouthpiece 2 and a positive pressure in the oral cavity is maintained such as to seal the soft palate in a closed position. The sealed soft palate creates an isolated nasopharynx such that NO gas may not enter the rest of the respiratory tract. Various methods and devices may be used to create the positive pressure in the oral cavity and seal the soft palate. Such methods and devices are generally described in U.S. Pat. Nos. 6,067,983; 6,715,485; U.S. Publication No. 2004/0149289, and U.S. Publication No. 2004/0112378, each herein incorporated by reference in their entirety. In order to close the soft palate, a positive pressure differential should be established between the oral cavity and the nasal airway. This pressure differential is about 5 cm $H_2O$ to about 10 cm $H_2O$. In order to create the necessary pressure in the oral cavity, various resistive elements may be employed. The resistive element may be preferably placed on the expiratory port so that there is no resistance to breathing air into the lungs. The mouthpiece 2 may include this resistive element, which may be, for example, one or more baffle plates or an absorbing filter to absorb bacteria or viral agents. The mouthpiece 2 may also allow a patient to inhale and exhale through the oral cavity, using the ambient atmosphere as the air supply, or any other source of breathable air. The mouthpiece 2 may be made of any suitable material, such as a polymeric material.

Referring to FIG. 3, a subject places the mouthpiece 2 in his/her lips and fits the nasal interface 6 into one of his/her nostrils, while the outlet nostril is fitted with the one-way valve 15. The subject then exhales through the mouthpiece 2, the flow of which exhaled air is resisted by the resistive element such as to develop a positive pressure in the oral cavity of the subject sufficient to cause closure of the soft palate. The exhaled air, after passing over the resistive element, then may mix with ambient air via an outlet 12. Alternatively, mouthpieces may be designed to attach to an artificial air source, as a reservoir or a ventilator. Again, reference number 10 refers to the NO containing gas flow. The nasal interface 6 is connected to the control unit 4 via appropriate tubing 13.

A pressure monitor 7 may be operably connected with the mouthpiece to determine the oral cavity pressure. This pressure monitor provides appropriate signals to the controller for controlling the opening and closing of the control valve for the flow of NO containing gas to the nasal interface 6. The triggering event for opening the flow of NO containing gas to the nasal interface 6 preferably occurs when the oral cavity pressure is about 5 cm $H_2O$.

Suitable therapeutic volumes of NO containing gas may be delivered to a patient. For example, a total gaseous flow rate may be about 1 liter per minute. For example, if NO is first blended with air, the NO gas flowing from the NO gas source may be about 0.2 liter per minute, while the compressed air flow may be about 0.8 liter per minute. Since the injection of NO containing gas to the nasal interface is controllably timed to correlate with an exhalation event, the flowrate of about 1 liter per minute may not be a continuous flowrate, but rather represents the rate of the pulsed injection. Each pulse injection therefore, may last for about 1 to about 5 seconds. The injections may also be consecutive for about 3 to about 60 minutes.

Preferred Delivery During Inhalation

Another device for the nasal delivery of NO during inhalation is illustrated in FIG. 4. In this device, a nasal interface 16 (such as a nasal mask or nasal insert prongs) is provided to interface with the nose of a subject, while leaving the mouth unobstructed. On one side of the nasal interface 16 is a valve 17 that may connect the nasal interface 16 to a collapsible gas reservoir 18 capable of holding a small volume of gas. The volume of the gas reservoir 18 may be substantially equal to the nasopharynx volume or another suitable therapeutic volume of NO containing gas. This volume is estimated at about 20 to about 50 mL for an adult human patient. When the valve 17 opens, the patient may nasally inhale the amount of gas from the reservoir 18, which is only enough to fill the patient's nasopharynx. This volume may also be forced into the nasal passage through manually squeezing the collapsible reservoir or through another suitable force or pressure-based flow. The reservoir may be filled directly from a pressurized gas tank containing NO gas, or may be replenished with the NO containing gas by using a small pressurized canister 19 that injects a fixed volume on each injection. A fill port 20 connected to the valve 17 may have a one-way check valve that allows gas to enter the reservoir.

Using this device, the patient may freely breathe through her mouth without obstruction, but will not inhale the NO containing gas past the nasopharynx because of the controlled volume of NO containing gas being delivered through use of the reservoir.

If the patient exhales through her nose, only that amount of gas that was in the nasopharynx will re-fill the reservoir 18. Thus, the nasal cavities, nasopharynx and sinuses, will be bathed in the NO containing gas in this delivery method. The patient may also recycle the NO containing gas from the reservoir 18 to the nasopharynx through this mask-reservoir system for a period of time, such as about 5 minutes to about 60 minutes. A suitable series of deliveries over a period of time may be suitable to bathe the upper respiratory tract including the nasopharynx with a therapeutic amount NO containing gas.

In another embodiment, delivery of nitric oxide gas to the upper respiratory tract may be achieved through delivery that is coincidental with the inhalation of the subject. Breathable air from any source (e.g., ambient room air or ventilator carrying oxygen containing gas) may be directed to a nasal interface using techniques well known in the art. The inspiration and expiration flow rates of a spontaneous nasal breathing of a patient may be monitored using a flow sensor known in the art and, inspiration flow profiles can be determined for the patient's breathing. Inspiration flow profile of the breathable gas is the flow rate of the gas as a function of inspiration time. Nasal delivery of the NO containing gas, preferably added to the breathable gas stream through a Y-piece connector, may be timed to coincide with the end of patient's nasal inspiration.

During the early part of the subject's breath, the inhaled gas contains no nitric oxide. As the subject ends its inspiration, the NO containing gas is injected into the gas stream so that the NO containing gas is inhaled through the nasal cavity to the nasopharynx. The timing of this injection may be accomplished by waiting until after the inspiratory flow rate reaches a maximum and returns close to zero flow. Once a predetermined threshold on the deceleration of an inhalation is reached, the NO containing gas stream may be initiated and added through the Y-piece connector. The timed delivery based on a patient's inspiratory flow profile and the device for performing such delivery is exemplified and described in U.S. Pat. No. 6,581,599 issued to one of the applicants and is incorporated by reference in its entirety as if fully set forth herein.

In the embodiments described to deliver the nitric oxide containing gas at the end of an inspiration, the concentration of the gas delivered may be slightly higher than the desired concentration for therapeutic effectiveness to account for the dilution by the breathable air flowing into the nose. For example, therapeutic concentrations of nitric oxide in the nitric oxide containing gas may be about 160 to 400 ppm. In order to meet the therapeutic level in certain embodiments, a delivery concentration of the nitric oxide should be increased by about 10 percent to account for dilution with breathable gas. For example, the delivery gas should contain concentrations of nitric oxide of about 175 to 440 ppm. These values of nitric oxide containing gas may be delivered to a patient near the end of their inspiration, wherein the patient is breathing at a flow rate of about 1 liter per minute. For example, delivered nitric oxide containing gas having a concentration of about 200 ppm at 9 liter per minute would be reduced to a concentration of about 180 ppm in the upper respiratory tract when diluted by the breathable air. As another example, a pulse of about 0.3 to 0.5 seconds of nitric oxide would deliver 50 to 80 milliliters of nitric oxide into the nose at a volume sufficient to fill only the nasopharynx.

Alternative triggering of the NO flow into the breathable gas stream can also be accomplished by measuring and modeling the patient's inspiration profile for a number of previous breaths. NO flow is then initiated on a subsequent breath based upon a predicted timing of the patient's breathing to flow NO only at the end of inspiration so that only the nasopharynx is filled. Yet another alternative method of determining the point to initiate the NO flow is by measuring the volume inspired by the patient, which can be calculated based on the flow rate and elapsed time of flow of the breathable gas. At the volume before reaching the end of inspiration whereby the NO flow would fill the nasopharynx, the NO gas would then begin its flow.

The above methods are preferably performed through the use of a control module, preferably a controller such as a computer microprocessor with associated logic (firmware or software), that may time the release of the nitric oxide containing gas to the nasal interface. The timing may be at the end of the mammal's inspiration, at a predetermined or premeasured time. Alternatively, the patient's inspiratory flow or volume may be measured and thus delivery will coincide with this measurement. In any timed delivery, the volume of NO containing gas is about equal to the patient's nasopharynx. This volume may be monitored or adjusted based on successive breaths.

In another embodiment, a pulse dose delivery or a bolus injection delivery of the NO containing gas may be used. The timing of the bolus injection may be correlated to the detection of a patient breath. Once a predetermined time has passed from breath detection, a bolus injection of the NO containing gas may be delivered to the upper respiratory tract.

In the inhalation methods of delivery, the NO containing gas is mixed or injected into the gas stream that is being nasally inhaled by a subject. By contrast, in the exhalation methods described above, the patient is breathing through its mouth. The nasal delivery of the NO containing gas may be "artificial" or forced, such as delivered through a pressurized system through the nostril(s) into the upper respiratory tract.

In the inhalation methods of delivery, the patient will not inhale the NO containing gas past the nasopharynx because of the controlled injection of NO containing gas. Hence, through the targeted delivery of the NO containing gas, the NO containing gas will only bathe and contact the upper respiratory system of the subject. Accordingly, there is little or no risk that the NO containing gas will reach beyond the nasopharynx into the lungs of the subject.

Devices to accomplish delivery methods during inhalation that are described above may include a delivery unit comprising a nasal interface (such as a nasal mask or nasal insert prongs) for fitting to a nostril of a subject, a source of breathable gas, and a nitric oxide containing source, and a control unit for delivering the gas. NO containing gas source may be a pressurized cylinder containing NO containing gas. After being optionally adjusted for delivery concentrations and pressure, the NO containing gas passes through tubing to a flow control valve. The flow control valve, which preferably is electronically controlled by the control unit, controls injection or addition of the NO containing gas into the gas stream flowing from the source of breathable gas to the nasal interface fitting into the nostril of a subject. The patient is allowed to nasally inhale and exhale this air from the air source, subject to the timed injection of the NO containing gas upon inhalation.

Upon timing with the patient's breathing or at a measured volume of the inspiration profile, the flow control valve opens and a jet of NO containing gas is added to breathable gas stream to be included as part of an inhalation.

The device may further include NO and $NO_2$ analyzers, that are well known in the art, to monitor the concentration of nitric oxide or nitrogen dioxide. Other safety devices known in the art such as $NO_2$ scavengers for exhaled gas may also be incorporated into the delivery devices described herein.

The NO containing gas may be dosed in several ways to supply a therapeutic amount. By the term "therapeutic amount" is meant, for purposes of the specification and claims, to refer an amount sufficient to kill or inhibit microorganisms in the upper respiratory tract. A flowrate of about 1 liter per minute of about 160 ppm nitric oxide to about 400 ppm nitric oxide may effectively decontaminate the upper respiratory tract of a subject. Therefore, about 1 liter per minute of about 160 ppm nitric oxide to about 400 ppm nitric oxide may be delivered to patients. Additionally, delivered gases having a slightly higher nitric oxide concentration, such as about 175 ppm to about 440 ppm, may be delivered to patients. These slightly higher concentrations account for dilution with breathable gas as explained above in the inhalation methods. Other suitable parameters for delivery, dosage, or NO exposure may be found in U.S. Pat. Nos. 6,793,644 and 6,432,077. In any delivery method, NO containing gas may be by bolus injection, or by pulse injection, systematically, for a period of time. Such suitable exposure times may be, for example, about 3 minutes to about 60 minutes of total NO exposure time.

Microcidal Effects of NO Gas

The delivery of a NO containing gas nasally to an upper respiratory area of a mammal may topically decontaminate the upper respiratory tract of microorganisms, such as viruses, bacteria, mycobateria, parasites, and fungi. This decontamination may be an effective treatment of nasopharyngeal infections and upper respiratory infections. While the delivery of the NO containing gas is isolated to the upper respiratory system including the nasopharynx, the decontamination of the upper respiratory tract of microorganisms greatly reduces risk of the spreading of infection to the lower respiratory tract and provides a preventative treatment of the respiratory system as a whole, including the lungs.

The dominant mechanism(s) whereby NO, known to be produced in response to stimulation of the calcium-independent inducible nitric oxide synthase, results in intracellular killing of mycobacteria has been described in U.S. patent application Ser. No. 09/762,152

Additionally, viruses may be susceptible to nitric oxide. While not wishing to be bound by theory, it appears that viruses may be susceptible to nitric oxide due to their unsophisticated detoxification pathways. Several possible mechanisms exist to explain the cidal and inhibitory effects of NO on viruses. First, metal ion based DNA deamination may be linked to the cidal effectiveness. NO may also play a dominant role in destructive hydroxyl radical formation. NO may interfere with viral replication through RNA reductase inhibition. NO may interfere with Hemagglutinin protein synthesis. NO may also interfere with virion release or maturation. Upon exposure to NO, infected cells exhibit reduced virion RNA release.

Several researchers have documented the antiviral effects of the NO molecule produced chemically by NO donors. For example, cells infected with influenza virus A/Netherlands/18/94 were treated with NO, an experiment described in Rimmelzwaan, et. al., "Inhibition of Influenza Virus Replication by Nitric Oxide," J. Virol. 1999; 73:8880-83, herein incorporated by reference in its entirety. Results show the effectiveness of NO as a preventive therapy to viral agents. Additionally, a study by Sanders, et. al. demonstrates the effectiveness of naturally produced NO by the body as an antiviral agent, particularly against human rhinovirus. See Sanders, et. al., "Role of Nasal Nitric Oxide in the Resolution of Experimental Rhinovirus Infection," J. Allergy Clin, Immunol. 2004 April; 113(4):697-702, herein incorporated by reference in its entirety.

Nasal Resistance Testing Following NO Exposure

Nitric oxide is known to have several biophysical properties, of which two important ones are its relaxation effects on blood vessels and its ability to kill microorganisms. With the approach of using exposure of the nasopharynx to NO gas to kill microorganisms was the question of whether it would have an adverse effect on the vascular tone of the nasal vessels that might preclude its therapeutic use because it might dilate the vessels and obstruct the nasal passage.

To test for this untoward effect, a normal volunteer was treated with 160 ppm NO gas using one of the methods described (1 liter per minute flowed up one nostril and out the other through a check valve during subject exhalation against a 5 cm $H_2O$ resistor) for 15 minutes. Prior to the treatment, baseline measurements of right and left nasal resistance were performed using a Jaeger rhinometer. The rhinometer measures the differential pressure across each of the nostrils being tested with a pressure sensor port measuring the pressure at the entrance of the nostril being tested and by occluding the non-tested nostril with pressure sensing line, measures the pressure at the back of the open nostril being tested. Each nostril was tested separately.

Following the 15 minute exposure, resistance of each nostril was measured and again at 30 minutes. The results of that experiment demonstrated that there was no change in overall nasal resistance and that the changes within each nostril was less than what is considered clinically significant and that the changes follow the normal diurnal variation between higher and lower resistances of the nasal passages. This supports that the NO produced no changes to nasal vasculature that would effect resistance to airflow.

While embodiments of the present invention have been shown and described, various modifications may be made without departing from the scope of the invention. The invention, therefore, should not be limited, except to the following claims, and their equivalents.

What is claimed is:

1. A nasal delivery device for delivering nitric oxide containing gas to an upper respiratory tract of a mammal, said device comprising:
 a source of nitric oxide containing gas;
 a nasal interface adapted to provide fluid communication between the source of nitric oxide containing gas and a first nostril of the mammal;
 a flow-control valve for controlling the flow of the nitric oxide containing gas from the source to the mammal;
 a one-way valve operable to be inserted into a second nostril of the mammal; and
 a mouthpiece comprising a resistive element operable to close the soft palate of the mammal.

2. The nasal delivery device of claim 1, wherein the nasal interface comprises a nosepiece operable to be inserted into the first a nostril of a mammal.

3. The nasal delivery device of claim 1, further comprising a pressure monitor operable to detect a pressure within an oral cavity of the mammal.

4. The nasal delivery device of claim 3, further comprising a controller with logic such that the flow control valve is opened when a threshold pressure is detected in the oral cavity of the mammal.

5. The nasal delivery device of claim 3, wherein the pressure monitor is operably connected to the mouthpiece.

6. The nasal delivery device of claim 1, further comprising a gas blender.

7. The nasal delivery device of claim 1, wherein the supply unit further comprises an NO analyzer.

8. The nasal delivery device of claim 1, wherein the supply unit is operable to deliver about 1 liter per minute of the nitric oxide containing gas.

9. The nasal delivery device of claim 1, wherein the one-way valve is operable to restrict inward flow upon delivery of the nitric oxide containing gas.

10. The nasal delivery device of claim 1, wherein the one-way valve is operable to allow the nitric oxide containing gas to exit the upper respiratory tract.

11. The nasal delivery device of claim 1, wherein the resistive element operable to provide at least about 5 cm $H_2O$ pressure in an oral cavity of the mammal.

12. The nasal delivery device of claim 1, further comprises a collapsible reservoir.

13. The nasal delivery device of claim 12, wherein collapsible reservoir has a volume that is substantially equal to the volume of the upper respiratory tract of the mammal.

14. The nasal delivery device of claim 13, wherein the volume of the collapsible reservoir is about 20 mL to about 50 mL.

15. A nasal delivery device for delivering a nitric oxide containing gas to an upper respiratory tract of a mammal, said device comprising:
 a collapsible reservoir comprising nitric oxide containing gas and having a volume substantially equal to the volume of the upper respiratory tract of the mammal;
 a nasal interface adapted to provide fluid communication between a nose of the mammal and the collapsible reservoir; and
 a control valve for controlling the delivery of the nitric oxide containing gas from the collapsible reservoir to the nasal interface.

16. The nasal delivery device of claim 15, wherein the volume of the collapsible reservoir ranges from about 20 mL to about 50 mL.

17. The nasal delivery device of claim 16, further comprising a fill port for filling the collapsible reservoir with nitric oxide containing gas from a source of nitric oxide gas.

18. The nasal delivery device of claim 15, wherein the nasal interface is a nasal mask operable to be placed around the nose of the mammal.

19. The nasal delivery device of claim 15, wherein the nasal interface is a nosepiece operable to be inserted into at least one nostril of a mammal.

20. The nasal delivery device of claim 19, wherein the nosepiece comprises an insert operable to seal the nostril of the mammal.

21. A nasal delivery device for delivering a nitric oxide containing gas to an upper respiratory tract of a mammal, the device comprising:
 a source of breathable gas connected via tubing to a nasal interface for providing a gas stream of breathable gas to the mammal nasally;
 an inspiration flow profile sensor that measures the inspiration flow profile of the inspiration breath of the mammal;
 a source of nitric oxide containing gas operably in fluid communication with the gas stream of the breathable gas;
 a flow controller located between the a source of nitric oxide containing gas and the gas stream for releasing nitric oxide containing gas to the nasal interface;
 a controller for triggering the release of nitric oxide containing gas to the nasal interface at a predetermined time close to the end of the mammal's inspiration and at a flow rate that confines the nitric oxide containing gas in the upper respiratory tract of the mammal.

22. The nasal delivery device of claim 21, wherein the predetermined time is a time after the inspiratory flow rate reaches maximum and returns to close to a zero inspiratory flow rate.

23. The nasal delivery device of claim 21, wherein the nasal interface is a nosepiece operable to be inserted into at least one nostril of the mammal.

* * * * *